United States Patent
Ballinger, Jr. et al.

(10) Patent No.: US 9,999,220 B2
(45) Date of Patent: Jun. 19, 2018

(54) METHOD FOR REPELLING RODENTS

(71) Applicant: Arkion Life Sciences, LLC, New Castle, DE (US)

(72) Inventors: Kenneth E. Ballinger, Jr., Kennett Square, PA (US); Scott John Werner, Wellington, CO (US)

(73) Assignees: THE UNITED STATES OF AMERICA, AS REPRESENTED BY THE SECRETARY OF AGRICULTURE, Washington, DC (US); ARKION LIFE SCIENCES, LLC, New Castle, DE (US)

( * ) Notice: Subject to any disclaimer, the term of this patent is extended or adjusted under 35 U.S.C. 154(b) by 0 days. days.

(21) Appl. No.: 14/595,718

(22) Filed: Jan. 13, 2015

(65) Prior Publication Data

US 2015/0196026 A1   Jul. 16, 2015

Related U.S. Application Data (60) Provisional application No. 61/926,546, filed on Jan. 13, 2014, provisional application No. 62/042,524, filed on Aug. 27, 2014, provisional application No. 62/043,529, filed on Aug. 29, 2014, provisional application No. 62/083,551, filed on Nov. 24, 2014.

(51) Int. Cl.
    *A01N 35/06*   (2006.01)
(52) U.S. Cl.
    CPC .................................. *A01N 35/06* (2013.01)
(58) Field of Classification Search
    None
    See application file for complete search history.

(56) References Cited

U.S. PATENT DOCUMENTS

| | | | |
|---|---|---|---|
| 2,547,722 A | | 4/1951 | Stewart |
| 3,663,253 A | | 5/1972 | Stone |
| 5,464,625 A | | 11/1995 | Nolte et al. |
| 5,549,902 A | | 8/1996 | Preiser et al. |
| 5,672,352 A | | 9/1997 | Clark et al. |
| 5,885,604 A | * | 3/1999 | Ballinger, Jr. ........... A01C 1/06 424/405 |
| 5,922,774 A | * | 7/1999 | Winslow ................ A01N 35/06 514/569 |

(Continued)

FOREIGN PATENT DOCUMENTS

| | | |
|---|---|---|
| EP | 0152852 | 8/1985 |
| GB | 1601226 | 10/1981 |

(Continued)

OTHER PUBLICATIONS

Werner et al., Applied Animal Behaviour Science 135 (2011) 146-153.*

(Continued)

*Primary Examiner* — Karl J Puttlitz
(74) *Attorney, Agent, or Firm* — McCarter & English, LLP (57) ABSTRACT

The present disclosure relates to the use of polycyclic quinones, and particularly, anthraquinones, to non-lethally repel rodents from consuming or otherwise damaging vegetation, private property, man-made structures, or agricultural products in the field and in storage. Further, the invention shows use as a protection strategy for various other products used as a food source by certain rodents.

20 Claims, 4 Drawing Sheets

(56) References Cited

U.S. PATENT DOCUMENTS

| | | | | |
|---|---|---|---|---|
| 6,328,986 | B1 * | 12/2001 | Ballinger, Jr. | ........... A01C 1/06 |
| | | | | 424/405 |
| 6,436,423 | B1 | 8/2002 | Ballinger, Jr. et al. | |
| 7,488,493 | B2 * | 2/2009 | Ballinger, Jr. | ......... A01N 37/02 |
| | | | | 424/405 |

FOREIGN PATENT DOCUMENTS

| | | |
|---|---|---|
| JP | 56-83408 | 7/1981 |
| WO | 9737540 | * 10/1997 |

OTHER PUBLICATIONS

Werner, Scott J., et al., "Anthraquinone Repellent to Reduce Take of Non-Target Birds from Zinc Phoshide Rodenticide Applications", Applied Animal Behaviour Science, vol. 135, 2011, pp. 146-153.
International Search Report and Written Opinion based on co-pending International Application No. PCT/US2015/11193, dated Mar. 27, 2015, 8 Pages.
Animal Physiology: Adaptation and Environment, Fourth Edition, Chapter 13, Information and Senses, pp. 1-6.
Douglas, R.H., et al., The Spectral Transmission of Ocular Media Suggests Ultraviolet Sensitivity is Widespread Among Mammals, Proceedings of the Royal Society of London B, 2014, vol. 281, pp. 1-9.

* cited by examiner

METHOD FOR REPELLING RODENTS

CROSS-REFERENCE TO RELATED APPLICATIONS

This application claims priority to U.S. Provisional Application No. 61/926,546, filed Jan. 13, 2014, U.S. Provisional Application No. 62/042,524, filed Aug. 27, 2014, U.S. Provisional Application No. 62/043,529, filed Aug. 29, 2014 and U.S. Provisional Application No. 62/083,551, filed Nov. 24, 2014, the contents of each are incorporated herein by reference in their entirety.

FIELD OF THE TECHNOLOGY

The invention is directed to the novel discovery that polycyclic quinones, such as anthraquinones, and specifically the 9,10 anthraquinone family of compounds, are selective, non-lethal rodent repellents. More particularly, this invention is directed to the feature that polycyclic quinones are particularly effective in repelling certain rodents from consuming or otherwise damaging agricultural products, crops, vegetation, and man-made structures.

BACKGROUND

Rodents can be a real annoyance and even a danger. These uninvited creatures consume everything, from vegetables to breadcrumbs, spreading bacteria and pathogens in the process. Rodents also cause major damage to stored crops and agricultural infrastructure. In areas where natural predators no longer occur, they become bold enough to venture out into orchards where they consume and carry away surprising quantities of crops.

They contaminate food and frequented areas with feces, urine, and hair. They carry diseases, such as spirochetal jaundice and murine typhus. According to the Centers for Disease Control and Prevention: Worldwide, rats and mice spread over 35 diseases. These diseases can be spread to humans directly, through handling of rodents, through contact with rodent feces, urine, or saliva, or through rodent bites. Diseases carried by rodents can also be spread to humans indirectly through ticks, mites or fleas that have fed on an infected rodent.

Getting rid of rodents can be a nuisance as well, to the earth, and to the health and safety of the indoor environment. Repellents may be used to non-lethally deter offending rodents. Current agronomic practices using exclusion such as wire fencing is limited in effectiveness and is expensive to apply. Poison bait is effective but limited to the area in which it is used and restricted in application because of non-target lethal effects. Both natural and chemical-based repellents are commercially available and vary in effectiveness. The smells of some plants, such as eucalyptus, wormwood and mint, are unattractive to rodents. However, they usually are minimally effective in repelling rodents.

Sound-based repellents are capable of emitting sound at a register too high for humans to recognize. These sounds are thought to be disconcerting to rodents and are intended to prevent them from infesting the area around them. However, sound-based repellents have shown limited effectiveness.

Repellents generally work by taking advantage of an animal's natural aversion to something, and often the thing chosen is something that the animal has learned to avoid (or instinctively avoids) in its natural environment. Chemical repellents mimic natural substances that repel or deter animals, or they are designed to be so irritating to a specific animal or type of animal that the targeted animal will avoid the protected object or area. Some chemical repellents combine both principles. Repellents fall into two main categories, odor and taste.

There remains a continued need for a reliable and economical method to non-lethally deter rodents from visiting uninvited locations or otherwise becoming a nuisance in such manner that neither the environment nor the rodents are harmed.

SUMMARY OF THE INVENTION

The present invention relates to a method for repelling rodents wherein the method comprises applying an effective amount of a polycyclic quinone to a substrate, whereby the effective amount of said composition results in 15%-85% rodent repellency from said surface.

The present invention relates to a method for repelling rodents wherein the method comprises applying an effective amount of a polycyclic quinone to a substrate, wherein the effective amount of polycyclic quinone is from about 0.5% to about 10% by weight of the substrate.

The present invention relates to a method for repelling rodents wherein the method comprises applying an effective amount of a polycyclic quinone to a substrate, wherein the polycyclic quinone is applied by application of about 5 pounds to about 40 pounds of polycyclic quinone per acre.

The present invention relates to a method for repelling rodents wherein the method comprises applying an effective amount of a polycyclic quinone to a substrate, wherein the polycyclic quinone is applied at a level ranging from 200-2000 grams/sq. meter.

DETAILED DESCRIPTION

The useful application of this invention is in providing a non-toxic substance that protects valuable agricultural products. In a preferred embodiment, the disclosure is directed to the use of polycyclic quinone based repellents, and in particular, an anthraquinone-based rodent repellent (Avipel®, a.i. 50% 9,10-anthraquinone; Arkion Life Sciences, New Castle, Del.). These inventive repellents can be used at a concentration range of 0.5%-10% or greater by weight of polycyclic quinone, and any ranges in between. In a further preferred embodiment, the concentration range of polycyclic quinone is 0.5-4%, 0.5-3%, 0.5-2%, 0.5-1%, 1-5%, 1-4%, 1-3%, 1-2%, 1-10%, 2-10%, 3%-10%, 4%-10%, 5%-10%, 6%-10%, 7%-10%, 8%-10% or 9%-10% by weight of polycyclic quinone.

It was found that repellent compositions containing polycyclic quinones can provide at least or more than about 15%, 16%, 17%, 18%, 9%, 20%, 21%, 22%, 23%, 24%, 25%, 26%, 27%, 28%, 29%, 30%, 31%, 32%, 33%, 34%, 35%, 36%, 37%, 38%, 38%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or 85% repellency. These values can also be used to form ranges, such as, for example, from about 15% to about 85% repellency, with preferred ranges for particular rodent families ranging from about 20-50%; 25-40%; 40-55%; and 55-85%. The percent repellency is based on the percentage of the treated item which is not consumed by the animal. For example, 100% repellency indicates that the animal did not consume any of the treated item, and 50% repellency indicates that the animal consumed half of the control amount.

In certain embodiments it is helpful for the polycyclic quinones to be incorporated into applicable formulations that are designed for appropriate application to desired surfaces for targeted for rodent repellency.

In certain embodiments, the invention is applicable the entire Rodentia family. In alternative embodiments, the invention is application to one or more of, or any combination of, mice and voles, or field mice and meadow mice (Cricetidae); house mice, wood mice, black rats and brown rats (Muridae); deer mice (*Peromyscus*); ground squirrels, tree squirrels, flying squirrels, marmots and prairie dogs (Sciuridae)); pocket gophers (Geomyidae); mountain beaver (Aplodontidae); kangaroo rats, kangaroo mice and pocket mice (Heteromyidae); beavers (Castoridae); scaly-tailed squirrels (Anomaluridae); springhaas (Pedetidae); mole rats (Spalacidae and Bathyergidae); bamboo rats (Rhizomyidae); dormice (Gliridae, Platacanthomyidae and Seleviniidae); jumping mice (Zapodidae); jerboas (Dipodidae); porcupines (Hystricidae and Erethizontidae); cavies (Caviidae); capybara (Hydrochoeridae); pacaranas (Dinomyidae); agoutis and pacas (Dasyproctidae and Agoutidae); chinchillas and vizcachas (Chinchillidae); hutias (Capromyidae); nutria (Myocastoridae); hedge rats and octodonts (Octodontidae); tuco-tucos (Ctenomyidae); *chinchilla* rats (Abrocomidae); spiny rats (Echimyidae); cane rats (Thryonomyidae); dassie rats (Petromuridae); spring hare (Pedetidae) and gundis (Ctenodactylidae). Murinae (Old World rats) and the family Cricetinae (New World rats) both of the order Rodentia; black rat (*Rattus rattus*); brown rat (*Rattus norvegicus*); kangaroo rat (*Dipodomys deserti*); musk rat (*Ondatra zibethica*); pack rat (*Neotoma*); wood rat; sand rat; gerbil; water rat, water vole (*Hydromys chrysogaster*); House mouse (*Mus musculus*); Naked mole rat (*Heterocephalus glaber*); Eurasian red squirrel (*Sciurus vulgaris*); Long-tailed *chinchilla* (*Chinchilla lanigera*); Guinea pig (*Cavia porcellus*); Coypu (*Myocastor coypus*); Capybara (*Hydrochoerus hydrochaeris*); gundis (Hystricomorpha; Ctenodactylus); brush-tailed porcupines (*Atherurus*); mountain degus (*Octodontomys*); North American porcupines (*Erethizon*); guinea pigs (*Cavia*); Sciuromorpha; mountain beavers (*Aplodontia*); New World flying squirrels (*Glaucomys*); chipmunks (*Tamias*); beavers (Castorimorpha; Castor); kangaroo rats (*Dipodomys*); pocket gophers (*Thomomys*); Myodonta; Muroidea; deer mice (*Peromyscus*); true mice (*Mus*); Dipodoidea; birch mice (*Sicista*); jumping mice (*Zapus*); pygmy jerboas (*Cardiocranius*); springhares (Pedetscidae); true gophers (Geomyidae); Laotian rock rat (incertae sedis Diatomyidae); African mole rats (Bathyergidae); giant hutias (Heptaxodontidae); chinchillas, viscachas (Chinchillidae); mouse-like hamsters (Calomyscidae); hamsters, New World rats and mice, muskrats, voles, lemmings (Cricetidae); crested rat (Muridae); climbing mice, rock mice, white-tailed rat, *Malagasy* rats and mice (Nesomyidae); mole rats, bamboo rats, zokors (Spalacidae); and spiny dormice (Platacanthomyidae) among others.

As set forth in more detail in the examples, the percent repellency can vary from species to species within the Rodential family. For instance, 0.5-4% anthraquinone effectively repelled Prairie Dogs (Sciuridae) at a repellency rate of 24-37%, while at 0.5-2% anthraquinone Voles (Cricetidae) and Ground Squirrels (*Urocitellus* spp.) were repelled at rates of 58-84% and 40-56% respectively. In accordance with the examples provided herein, one skilled in the art can readily determine the most effective dosage concentration of polycyclic quinone to be used to repel the particular rodent of concern.

The polycyclic quinone can be applied to a virtually any surface from which rodent repellency is desired. Agricultural products, and particularly, crops are obviously a primary target of rodents. Some examples of agricultural products as used in this application include, but are not limited to sugar cane, maize, rice, wheat, potatoes, sugar beet, soybeans, cassava, tomatoes, barley, cereals, vegetables, melons, roots, tubers, milk, fruit, meat, oilcrops, fish, eggs, pulses, and vegetable fiber. The polycyclic quinone repellent composition of the invention can be applied to the agricultural products themselves in the field or the polycyclic quinone repellent composition can also be applied to the ground and ground coverings beneath which roots, tubers and other subsoil agricultural crops grow. In a preferred embodiment, the agricultural products can be treated via spray application of polycyclic quinone at a range of about 5-40 pounds per acre.

The polycyclic quinone repellent can be applied to the agricultural products once contained in storage. The polycyclic quinone repellent composition can also be applied to the storage containers themselves and the area surrounding the vicinity of the storage containers, such as the storage facility in general, shelving, pallets, flooring, walls, insulation, roofing, etc. In such cases, it is preferred that the polycyclic quinone be applied at a level ranging from 200-2000 grams/sq. meter, and any amount or range in between.

The polycyclic quinone can also be applied directly to vegetation in general. Vegetation as used in this application refers to assemblages of plant species. Some general examples of vegetation include agricultural and horticultural systems, natural and man-made grasslands, forests, trees, plants, turf, etc. In a preferred embodiment, the vegetation can be treated via spray application of polycyclic quinone at a range of about 5-40 pounds per acre.

In a preferred application, the polycyclic quinone is applied to agricultural crop seeds. Examples of agricultural crop seeds include, but are not limited to, corn, milo (sorghum), rice, soybean, wheat, rye, oats, barley, canola and sunflower. The polycyclic quinone can be applied by any method and at any concentration that is effective at achieving rodent repellency. The polycyclic quinone compounds of the invention can be applied at levels of about 0.5% to about 10% by weight of the seed, and any ranges in between. In one embodiment, the polycyclic quinone is applied at a level of about 0.5% by weight to about 5% by weight of the seed. In alternative embodiments, the polycyclic quinone can be applied at a level of 0.5% by weight to about 2% by weight of the seed or at a level of about 0.5% by weight to about 1% by weight of the seed. Alternatively, the polycyclic quinone can be applied at a level of about 1% by weight to about 5% by weight of the seed, or at a level of about 2% to about 5%.

The polycyclic quinone of the invention can also be applied to emerging seedlings of agricultural plants. Examples of agricultural crop seeds include corn, milo (sorghum), rice, soybean, wheat, rye, oats, barley, canola and sunflower. In such a case, the polycyclic quinone can be applied in any manner and quantity that is effective in repelling rodents. In one application, the polycyclic quinone is applied via spray application of 40 pounds or less of polycyclic quinone per acre. In a preferred application, the polycyclic quinone is applied to emerging seedlings via spray application of a range of about 5-40 pounds per acre, and any amount or range in between can also be effective. The polycyclic quinone of the invention can also be applied to fully grown agricultural plants, and in this application the polycyclic quinone can also be applied in any manner and quantity that is effective in repelling rodents. In one embodiment, the polycyclic quinone is applied via spray application of 40 pounds of polycyclic quinone or less per acre. In a preferred application, the polycyclic quinone is applied to emerging seedlings via spray application of a range of about 5-40 pounds per acre, and any amount or range in between may be effective. In certain cases, it may be most effective to apply the polycyclic quinone to the ground and ground coverings beneath which roots, tubers and other subsoil agricultural crops grow at a preferred rate that achieves rodent repellency.

In an alternative embodiment, the polycyclic quinone can be applied to the trunks of trees (for example, to prevent girdling). In such applications, the polycyclic quinone can be applied in any matter that is effective in repelling rodents. It is typically preferred that the polycyclic quinone be applied at a level ranging from 200-2000 grams/sq. meter, and any amount or range in between. A more preferred range would be 400-800 grams/sq. meter, and an even more preferred range would be 500-700 grams/sq. meter. In a preferred application, the polycyclic quinone is applied by a painting application that creates a barrier of polycyclic quinone concentration around the trunk to a height of about 3 feet or less.

The polycyclic quinone can be applied to structural surfaces such as private property and man-made structures. Examples of structural surfaces include buildings, roofings, insulation, pavement, roads, driveways, and any other man-made structure. It is typically preferred that the polycyclic quinone be applied to solid surfaces at a level ranging from 200-2000 grams/sq. meter, and any amount or range in between. A more preferred range would be 400-800 grams/sq. meter, and an even more preferred range would be 500-700 grams/sq. meter. Private property would include the land owned by a landowner and everything in it that is owned by the landowner. All sections of private property can be treated with the polycyclic quinone repellent composition of the invention if it is susceptible to rodent attention.

It is within the skill in the art to determine appropriate levels of polycyclic quinone that can be applied to result in effective rodent repellency, with direction provided in the examples. In addition, there are numerous methods for applying the polycyclic quinones of the invention, including but not limited to, arial spraying, ground based spraying, painting directly onto a trunk of a tree, spraying onto a seed then drying prior to planting, mixing a dry powder formulation with the seed directly during planting, spraying into the planting furrow (seed bed) in advance of adding the seed, addition to the irrigation system for the field, and hand spraying parts of a tree or bush. Pretreatment of a seedling prior to planting may include a dipping process or a small focused spraying post planting. More description regarding effective formulations and application methods are provided below and in the examples.

The following table summarizes preferred ranges of polycyclic quinone based upon the application method being incorporated. This table is in no way intended to be limiting, other than to show some examples of preferred ranges of polycyclic quinone that are effective for rodent repellency.

TABLE 1

Polycyclic quinone formulations and application rates.

| Application | Rate |
| --- | --- |
| Powder application to seed | 0.5%-10% by weight |
| Air spray liquid formulation | 5-40 pound(s) a.i. per acre |
| Ground spray liquid formulation | 5-40 pound(s) a.i. per acre |
| Surface Treatment (e.g. painting) | 200-2000 grams per square meter |

Polycyclic Quinones
Composition

A wide variety of polycyclic quinones can be used in the invention. As used herein, the term "polycyclic quinone" refers to bicyclic, tricyclid and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm, by weight. Below is the chemical structure of the polycyclic quinone 9,10-anthraquinone:

However, as noted above, certain precursors of such PCQs can also be used in the invention, either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs that can be used in the invention are anthraquinone, 1,2-dihydroxy anthraquinone, 1,4-dihydroxy anthraquinone, naphthoquinone, anthrone(9, 10-dihydro-9-oxo-anthracene), 10-methylene-anthrone, phenanthrenequinone and the alkyl, alkoxy and amino derivatives of such quinones, 6,11-dioxo-1H-anthra[1,2-c] pyrazole, anthraquinone-1,2-naphthacridone, 7,12-dioxo-7, 12-dihydroanthra[1,2-b]pyrazine, 1,2-benzanthraquinone, 2,7-dimethylanthraquinone, 2-methylanthraquinone, 3-methylanthraquinone, 1-aminoanthraquinone and 1-methoxyanthraquinone. In addition, more complex polycyclic quinone compounds can be used, such as 2-carboxy-1,3,5,6,8-pentahydroxy-7-monosaccharide and other saccharides of anthraquinones or glucosamides and 2(1,3-dihydro-3-oxy-5-sulfo-2H-indol-2-ylidine)-2,3-dihydro-3-oxo-1H-indole-5-sulfonic acid, disodium salt. Of the foregoing cyclic ketones, anthraquinone and 1,4-dihydroxyanthraquinone are preferred because they appear to be more effective. Naturally occurring anthraquinones can be used as well as synthetic anthraquinones.

Other PCQs which can be used include insoluble anthraquinone compounds, such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxy-anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9-10) will result in the formation of the insoluble molecular anthrahydroquinone. Aerobic solutions will incur oxidation of the anthraquinones to anthraquinone. Thus, anthrahydroquinones will not exist for long periods of time in an aerated environment, such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

Physical Properties—Volatility, Water Solubility

It is important to the effectiveness of the invention that the PCQ, in whatever physical form it is applied, be persistent. That is, the applied active material must be able to resist erosion by wind and rain and other environmental forces to which the treated surface is exposed. For this reason, it is preferred (1) that the active form of the PCQ have a relatively low solubility in water so that it is not easily washed off the treated surfaces, and (2) that it have a relatively high melting temperature so that it does not undergo excessive evaporation or sublimation from the treated surfaces during exposure to high ambient temperatures. For these reasons, it is preferred that the active PCQ material has a solubility in water under ambient temperature conditions of no more than about 1000 ppm and preferably at least 10-200 ppm and that the melting temperature of the active PCQ component be at least about 150 C and preferably at least 200 C.

Even when the active PCQ material possesses the above-described preferred physical properties, the material may have poor persistence because it does not adhere well to the surface to which it is applied. This is a function of the different properties of the surface and the PCQ material. When this occurs, it is further preferred that the formulation contain a "sticking agent", i.e., a material which itself has good adhesion to the substrate and when mixed with the active material causes the PCQ to adhere to the substrate more firmly. Preferred sticking agents are aqueous polymer lattices, which upon evaporation of the water therefrom, form a polymeric mass which is highly adhesive to the plant surface and holds particles of the active material firmly on the plant or solid surface. Such sticking agents typically contain a small amount of surfactant dissolved in the aqueous phase.

Even though highly water-insoluble PCQ compounds are preferred, less insoluble compounds are nevertheless usable in the invention under conditions in which they are not unduly exposed to conditions by which they are washed off. Furthermore, the use of water-resistant sticking agents can be used to mitigate the washing effect of heavy rains.

A distinct advantage of the PCQ compounds that have been tested for use in the invention is that they are essentially non toxic, i.e., they have an $LD_{50}$ of at least 2,000 mg/kg in rats and preferably an $LD_{50}$ in rats of 5,000 mg/kg or higher. Because of this low toxicity of PCQs, they are not toxic to most insects or to rodents, animals and humans. Moreover, the toxicity level is sufficiently low that any active material that becomes leached into the soil will not be detrimental to the normal constituents of fertile soil layers.

It is important to note that the source of the PCQ used for rodent repellency is an important criteria to ensure low toxicity. For example, applicants have registered with the U.S. EPA the PCQ known as 9,10-anthraquinone as a safe, non-toxic PCQ for use as a rodent repellent (see U.S. EPA Pesticide Fact Sheet for Anthraquinone, December 1998). It is within the scope of those having ordinary skill in the art to substitute other non-toxic PCQ's in place of anthraquinone for use in the present invention.

Polycyclic Quinone Rodent Repellent Formulations

The polycyclic quinone compositions of the invention can include the polycyclic quinone itself, but in many cases it is preferred that the polycyclic quinone compound be formulated into a composition that is suited well for its particular intended application. Below are provided various ingredients that may be used in formulating a polycyclic quinone containing composition that is effective for rodent repellency.

Coadjuvants

As used herein, the term "coadjuvant" refers to materials which have a bio-activity different than the polycyclic quinones themselves. Such materials include contact repellents, fungicides, pesticides, and mixtures thereof. Both liquid and solid coadjuvants can be used in conjunction with the PCQ's of the invention, depending on the manner of application. (See discussion below.) It should be noted, however, that the use of fungicides and pesticides as adjuvants may not be preferred because of the poisonous nature of such adjuvants.

An important class of coadjuvant for use in combination with the PCQs are trigeminal repellents, i.e., repellents which repel rodents when the rodent tastes the material. It has been found that terpene-based compounds are particularly useful for this purpose. Limonene, pinene and pulegone are terpenes which are preferred for this purpose. However, polymeric terpenes are also useful for this purpose, especially low molecular weight polymeric terpenes, which are sticky in character.

When terpenes are used as co-repellents with PCQs, they will ordinarily constitute a major part of the composition and the PCQs will constitute only a minor part. For example, composition comprising as little as 1% wt. PCQ in terpene (including polymeric terpenes) can be used effectively. Though still higher PCQ concentrations can be used, it will not be necessary to use more than about 10% wt. On the other hand, as little as 10% wt. terpene compound can be used, at least 30% being preferred to enhance the contact repellency properties.

Other trigeminal repellents, such as pepper and 2-hydroxyacetophenone, and methylanthranalate, can also be used in admixture with the PCQ and admixtures of PCQ with other trigeminal repellents.

Additives

As used herein, the term "additives" refers to materials which augment the effectiveness of the compositions of the invention, but which do not by themselves have bio-activity. These include such materials as surfactants, wetting agents, defoaming agents, extenders, sticking agents, penetrants, plasticizers, activators, spreading agents, diluents, odorants and the like.

As used herein, the term "surfactant" refers to a substance which serves as a wetting agent that lowers the surface tension of a liquid, allowing easier spreading, and lowers the interfacial tension between two liquids. Surfactants are usually organic compounds that are amphipathic, meaning they contain both hydrophobic groups (their "tails") and hydrophilic groups (their "heads"). Therefore, they are typically sparingly soluble in both organic solvents and water. Surfactants reduce the surface tension of water by adsorbing at the air-water interface. They also reduce the interfacial tension between oil and water by adsorbing at the liquid-liquid interface. Many surfactants can also assemble in the bulk solution into aggregates that are known as micelles. When micelles form in water, their tails form a core that is like an oil droplet, and their (ionic) heads form an outer shell that maintains favorable contact with water. When surfactants assemble in oil, the aggregate is referred to as a reverse micelle. In a reverse micelle, the heads are in the core and the tails maintain favorable contact with oil. Surfactants are particularly useful in accomplishing the wetting or penetration of solids by aqueous liquids and serve in the manner of detergent, emulsifying, or dispersing agents.

In certain embodiments of the invention, a "thickening agent" (also referred to herein as "thickener") may be used. The thickening agent is selected from the group consisting of an inorganic or organic thickener. Some examples of thickeners include fumed silica, clay, and polytetrafluoroethylene, fatty acid complexes of aluminum, lithium, calcium, calcium sulfonate, sodium, titanium, xanthan gum or the like, and combinations thereof.

An alcohol such as a glycol may be used in certain embodiments. Non-limiting examples of glycols include propylene glycol, butylene glycol, pentylene glycol, hexylene glycol, oligomers of ethylene glycol, oligomers of propylene glycol or mixtures thereof.

"Sticking Agents" (also referred to herein as "stickers") may also be used in the compositions of invention. A sticking agents is a material which itself has good adhesion to the targeted substrate and when mixed with the repellent of the invention, causes the repellent to adhere to the substrate more firmly. Examples of sticking agents include, for example, aqueous polymer lattices, which upon evaporation of the water therefrom, form a polymeric mass which is highly adhesive to a solid surface and holds particles of the active material firmly on such surface. Such latex sticking agents typically contain a small amount of surfactant dissolved in the aqueous phase. It is noted that any other sticking agent which causes or helps the repellent to adhere to the desired surface or substrate can be used in the invention.

When the PCQs are in powder form, they can be dispersed in a liquid media, especially water, and sprayed as a liquid suspension. On the other hand, when water-soluble precursors of the PCQs are used, they can be dissolved in water for dilution and then applied by spraying in the usual manner. The aeration, which occurs during spraying is sufficient to convert the soluble salt to the more active water-insoluble form. In both of these techniques either solid or liquid coadjuvants can be used. For example, water-soluble coadjuvants can be dissolved in the liquid medium or water-insoluble coadjuvant particles can be suspended in the liquid medium along with the PCQ and/or PCQ precursor.

It will be recognized from the foregoing discussion that not all of the PCQ coatings may be of suitable configuration. However, so long as a sufficient fraction of the coating is available to the rodents' nerve endings, the composition will effectively deter them from the surface. As mentioned above, access of the PCQ repellent to the oral sensors of the rodent may occur during preening of body parts which contain the repellent as a result of contact with the treated surfaces.

It will be recognized that other dispersion media than water can be used. For example, safe, degradable oils, such as vegetable oils, can be used. However, from the standpoint of safety and environmental health, it is much preferred to use water.

While this disclosure has been particularly shown and described with reference to example embodiments thereof, it will be understood by those skilled in the art that various changes in form and details may be made therein without departing from the scope of the invention encompassed by the appended claims.

EXAMPLES

Example 1

Repellent Efficacy of an Anthraquinone-based Repellent for Prairie Dogs (Sciuridae)

We conducted a concentration-response experiment with an anthraquinone-based repellent (Avipel®, a.i. 50% 9,10-anthraquinone; Arkion Life Sciences, New Castle, Del.) to determine anthraquinone repellency for black-tailed prairie dogs (*Cynomys ludovicianus*, N=44 males and females; Werner et al. 2011). During a 3-day pre-test, we offered one bowl (untreated whole corn) in individual cages at 08:00 h, daily. Prairie dogs were ranked based upon pre-test consumption and assigned to one of five treatment groups (n=8-9 prairie dogs per group) at the conclusion of the pre-test such that each group was similarly populated with subjects that exhibited high-low daily consumption. We randomly assigned repellent treatments among groups. During the 1-day test, we offered one bowl (repellent-treated whole corn) at 08:00 h. Consumption of treated corn seeds was measured (±0.1 g) at 08:00 h on the day subsequent to the test.

Figure 1:
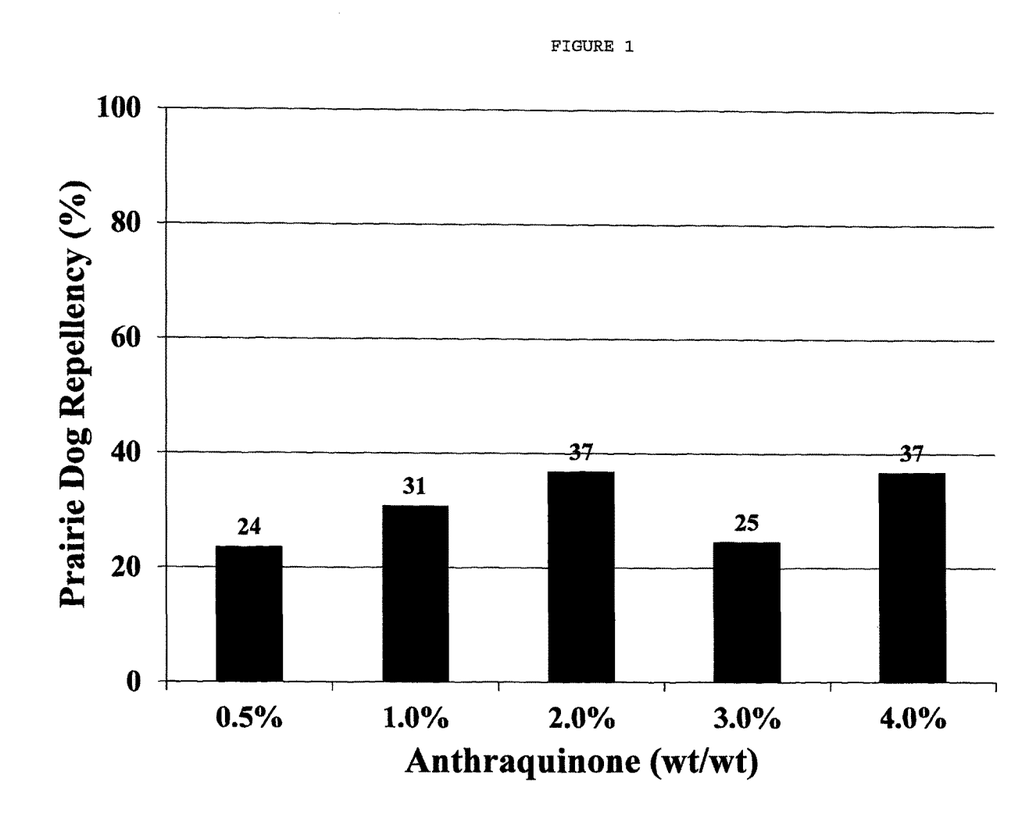
FIG. 1 is a bar graph depicting rodent repellency during a concentration-response experiment with black-tailed prairie dogs offered corn seeds treated with 0.5-4% anthraquinone set forth in Example 1.

We observed 24-37% repellency (FIG. 1) during our concentration-response experiment with black-tailed prairie dogs offered corn seeds treated with 0.5-4% anthraquinone (target concentrations; Werner et al. 2011).

Example 2

Repellent Efficacy of an Anthraquinone-based Repellent for Voles (Cricetidae)

We conducted a concentration-response experiment with an anthraquinone-based repellent (Avipel®, a.i. 50% 9,10-anthraquinone; Arkion Life Sciences, New Castle, Del.) to determine anthraquinone repellency for California (*Microtus californicus*, N=30 males and females). During a 3-day pre-test, we offered one bowl (untreated whole oats) in individual cages at 08:00 h, daily. Voles were ranked based upon pre-test consumption and assigned to one of three treatment groups (n=10 voles per group) at the conclusion of the pre-test such that each group was similarly populated with subjects that exhibited high-low daily consumption. We randomly assigned repellent treatments among groups. During the 1-day test, we offered one bowl (repellent-treated whole oats) at 08:00 h. Consumption of treated oats was measured (±0.1 g) at 08:00 h on the day subsequent to the test.

Figure 2:
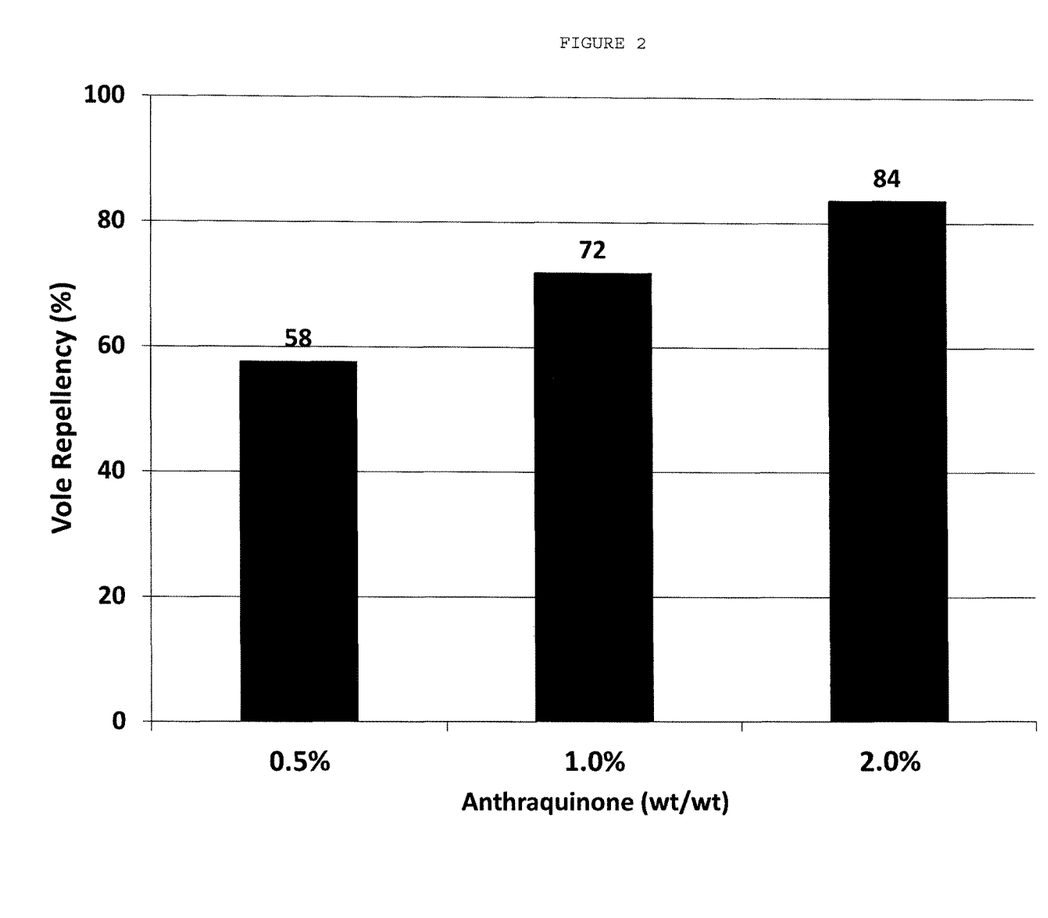
FIG. 2 is a bar graph depicting rodent repellency during a concentration-response experiment with California voles offered oats treated with 0.5-2% anthraquinone set forth in Example 2.

We observed 58-84% repellency (FIG. 2) during our concentration-response experiment with California voles offered oats treated with 0.5-2% anthraquinone (target concentrations).

Example 3

Repellent Efficacy of an Anthraquinone-based Repellent for Ground Squirrels (*Urocitellus* spp.)

We conducted a concentration-response experiment with an anthraquinone-based repellent (Avipel®, a.i.50% 9,10-anthraquinone; Arkion Life Sciences, New Castle, Del.) to determine anthraquinone repellency for Richardson's ground squirrels (*Urocitellus richardsonii*, N=28 males and females). During a 3-day pre-test, we offered one bowl (untreated whole oats) in individual cages at 08:00 h, daily. Ground squirrels were ranked based upon pre-test consumption and assigned to one of three treatment groups (n=9-10 squirrels per group) at the conclusion of the pre-test such that each group was similarly populated with subjects that exhibited high-low daily consumption. We randomly assigned repellent treatments among groups. During the 1-day test, we offered one bowl (repellent-treated whole oats) at 08:00 h. Consumption of treated oats was measured (±0.1 g) at 08:00 h on the day subsequent to the test.

Figure 3:
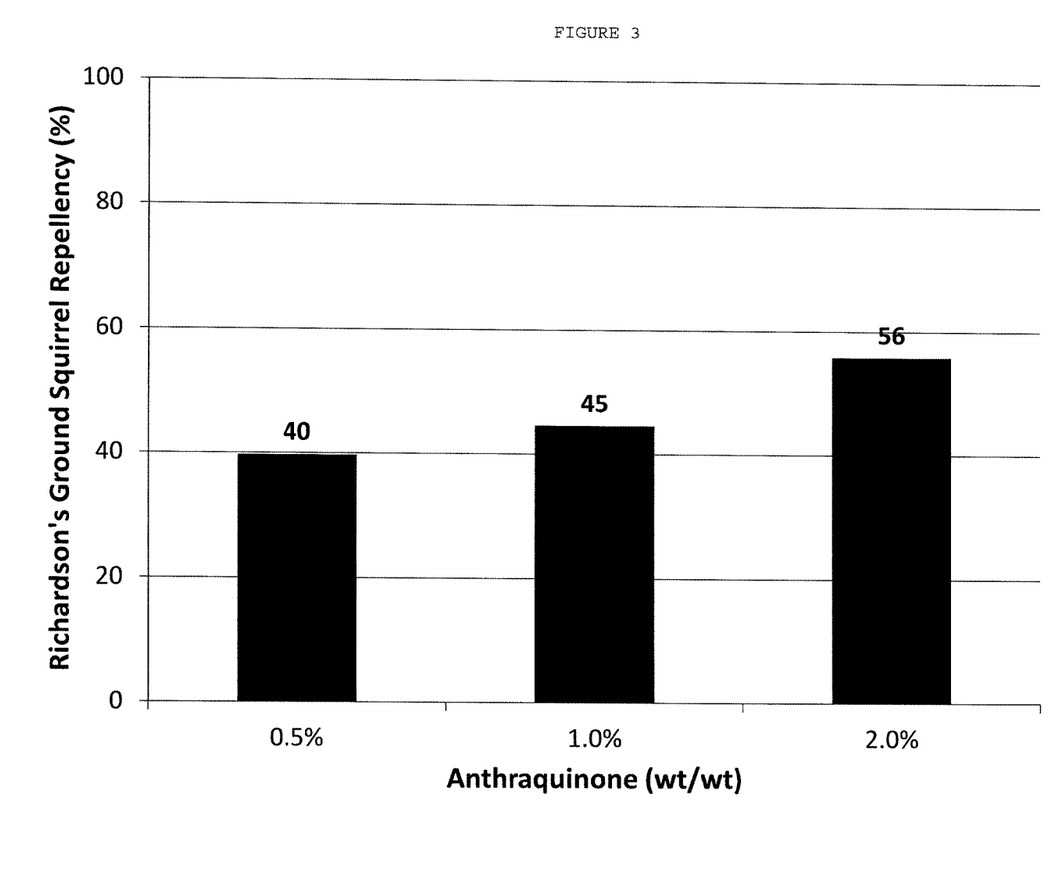
FIG. 3 is a bar graph depicting rodent repellency during a concentration-response experiment with Richardson's ground squirrels offered oats treated with 0.5-2% anthraquinone set forth in Example 3.

We observed 40-56% repellency (FIG. 3) during our concentration-response experiment with Richardson's ground squirrels offered oats treated with 0.5-2% anthraquinone (target concentrations).

Example 4

Rat Repellency Example

Anthraquinone is not a classic toxicant but a feeding study on Sprague-Dawley rats was done to determine effects of long term feeding where there was a single choice offered to rats over a 13 week period.

Anthraquinones was administered to four groups of 10 male and 10 female Sprague-Dawley rats/group at concentrations of 0, 500, 2000, or 7500 ppm (0, 40, 125, or 495 mg/kg/day in males; 0, 44, 150, or 661 mg/kg/day in females) for 4 consecutive weeks. Beginning with Week 5, the 500 ppm diet was reduced to 200 ppm resulting in lowering the doses to 11 and 16 mg/kg/day for males and females, respectively, through the end of the 13-week experimental period.

TABLE

| Dose Rate | Body Weight (G ± SD) | | | | Total Weight Gain | |
|---|---|---|---|---|---|---|
| PPM | Day 1 | Week 3 | Week 7 | Week 13 | Grams | % difference from control |
| Males | | | | | | |
| 0 | 253 ± 9.5 | 405 ± 18.7 | 510 ± 27.6 | 561 ± 34.5 | 308 ± 31.3 | |
| 500 | 252 ± 14.5 | 379 ± 26.4 | 471 ± 39.4 | 528 ± 47.4 | 275 ± 38.7* | −11% |
| 2000 | 250 ± 13.5 | 359 ± 23.7 | 443 ± 36.9 | 498 ± 43.0 | 247 ± 37.1** | −20% |
| 7500 | 250 ± 10.1 | 342 ± 20.2 | 425 ± 28.7 | 470 ± 37.9 | 221 ± 34.0** | −28% |
| Females | | | | | | |
| 0 | 193 ± 4.8 | 253 ± 10.9 | 298 ± 13.6 | 315 ± 15.3 | 122 ± 12.0 | |
| 500 | 185 ± 12.2 | 223 ± 12.4 | 254 ± 14.2 | 274 ± 15.0 | 89 ± 10.1** | −27% |
| 2000 | 188 ± 14.6 | 212 ± 14.2 | 238 ± 11.7 | 247 ± 16.3 | 59 ± 9.2** | −51% |
| 7500 | 189 ± 11.8 | 204 ± 22.0 | 226 ± 26.3 | 217 ± 27.7 | 29 ± 28.2** | −76% |

*$p \leq 0.05$
**$p \leq 0.01$

Results demonstrate a repellency effect causing lack of weight gain from inhibited feeding throughout the trial. While some repellency was observed at 500 ppm, effective repellency began at approximately 2000 ppm. Significant reduction in feeding with a single choice indicates a non-lethal repellency.

Example 5

Repellency Efficacy of an Anthraquinone-based Repellent for Deer Mice (*Peromyscus* spp.)

We conducted a concentration-response experiment with an anthraquinone-based repellent (Avipel®, a.i.50% 9,10-anthraquinone; Arkion Life Sciences, New Castle, Del.) to determine anthraquinone repellency for deer mice (*Peromyscus maniculatus*, N=34 males and females). During a 3-day pre-test, we offered one bowl (untreated whole oats) in individual cages at 08:00 h, daily. Deer mice were ranked based upon pre-test consumption and assigned to one of four treatment groups (n=8-9 mice per group) at the conclusion of the pre-test such that each group was similarly populated with subjects that exhibited high-low daily consumption. We randomly assigned repellent treatments among groups. During the 1-day test, we offered one bowl (repellent-treated whole oats) at 08:00 h. Consumption of treated oats was measured (±0.1 g) at 08:00 h on the day subsequent to the test.

Figure 4:
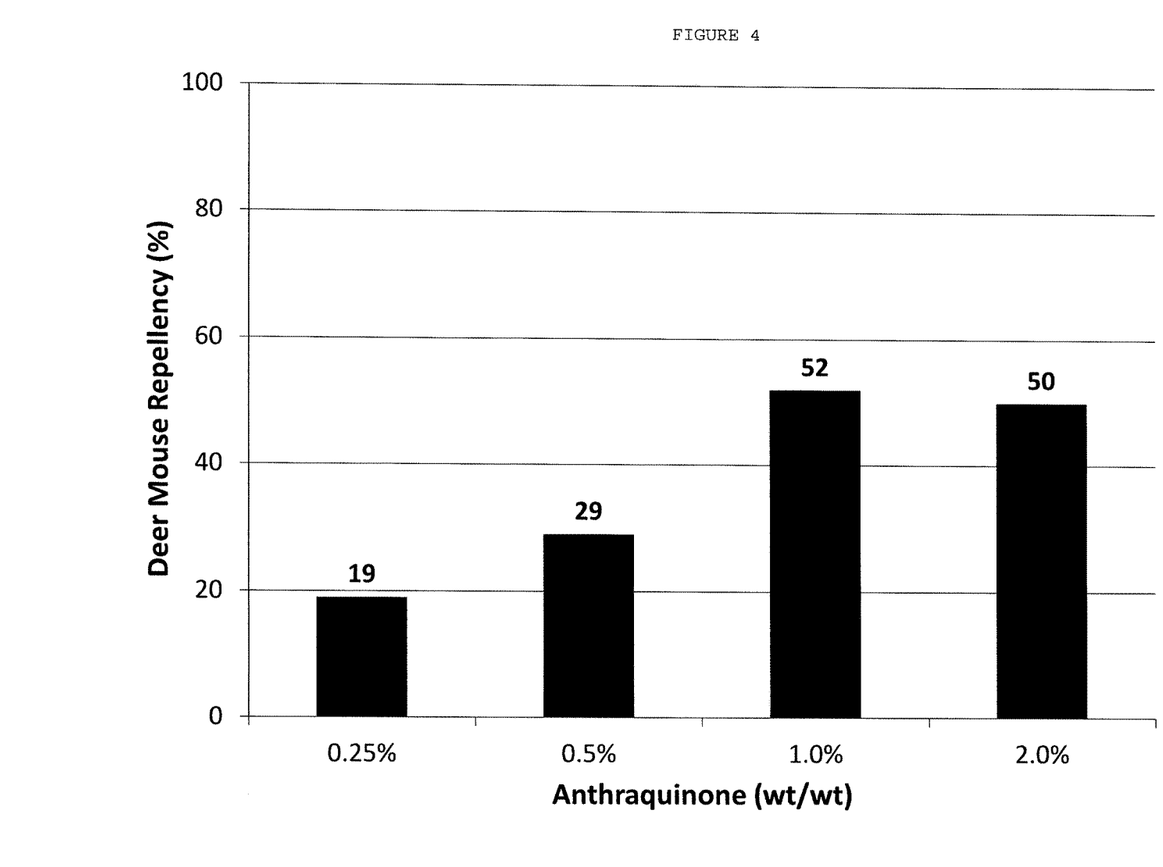
FIG. 4 is a bar graph depicting rodent repellency during a concentration-response experiment with deer mice offered oats treated with 0.25-2% anthraquinone set forth in Example 5.

We observed 19-52% repellency (FIG. 4) during our concentration-response experiment with deer mice offered oats treated with 0.25-2% anthraquinone (target concentrations).

Example 6

Formulation 1:
The below 9, 10 Anthraquinone formulation, which is effective for rodent repellency when applied to surfaces at the rates set forth in this application, is suitable for application to any solid or plant surface:

| | |
|---|---|
| AQ | 49-52% |
| Water | 35-43% |
| Propylene Glycol | 5% |
| Surfactants | 1-2% |
| Thickeners | 0.5-1% |
| Sticker | 0-5% |

Example 7

Formulation 2:
The below 9, 10 Anthraquinone formulation, which is effective for rodent repellency when applied to surfaces at the rates set forth in this application, is suitable for application to any solid or plant surface:

| | |
|---|---|
| AQ | 24-26% |
| Water | 68-70% |
| Proplyene Glycol | 5% |
| Surfactants | 1-2% |
| Thickeners | 1-2% |

Example 8

Formulation 3:
The below 9, 10 Anthraquinone formulation, which is effective for rodent repellency when applied to surfaces at the rates set forth in this application, is suitable for application to any solid or plant surface:

| | |
|---|---|
| AQ | 15-30% |
| Visual Mimic | 45%-30% |
| Water | 25-35% |
| Propylene Glycol | 2-3% |
| Surfactants | 1-3% |
| Thickeners | 1-3% |

We claim:

1. A method for repelling rodents, the method comprising applying a polycyclic quinone to a substrate at a level ranging from 200-2000 grams per square meter to create a polycyclic quinone barrier that provides a rodent repellency level of at least 80%, wherein the substrate comprises a structural surface.

2. The method of claim 1 wherein the polycyclic quinone is an anthraquinone.

3. The method of claim 2 wherein the anthraquinone is 9,10 anthraquinone.

4. The method of claim 1 wherein the substrate is selected from the group consisting of private property, man-made structures, buildings, the area surrounding the vicinity of a building structure, roofing, insulation, pavement, roads, driveways, flooring, walls, shelving, pallets and storage containers.

5. The method of claim 1 wherein the rodents are selected from the group consisting of the entire Rotentia family.

6. The method of claim 1 wherein the rodents are selected from the group consisting of mice and voles, or field mice and meadow mice (Cricetidae); house mice, wood mice, black rats and brown rats (Muridae); deer mice (*Peromyscus*); ground squirrels, tree squirrels, flying squirrels, marmots and prairie dogs (Sciuridae)); pocket gophers (Geomyidae); mountain beaver (Aplodontidae); kangaroo rats, kangaroo mice and pocket mice (Heteromyidae); beavers (Castoridae); scaly-tailed squirrels (Anomaluridae); springhaas (Pedetidae); mole rats (Spalacidae and Bathyergidae); bamboo rats (Rhizomyidae); dormice (Gliridae, Platacanthomyidae and Seleviniidae); jumping mice (Zapodidae); jerboas (Dipodidae); porcupines (Hystricidae and Erethizontidae); cavies (Caviidae); capybara (Hydrochoeridae); pacaranas (Dinomyidae); agoutis and pacas (Dasyproctidae and Agoutidae); chinchillas and vizcachas (Chinchillidae); hutias (Capromyidae); nutria (Myocastoridae); hedge rats and octodonts (Octodontidae); tuco-tucos (Ctenomyidae); *chinchilla* rats (Abrocomidae); spiny rats (Echimyidae); cane rats (Thryonomyidae); dassie rats (Petromuridae); spring hare (Pedetidae) and gundis (Ctenodactylidae); Murinae (Old World rats) and the family Cricetinae (New World rats) both of the order Rodentia; black rat (*Rattus rattus*); brown rat (*Rattus norvegicus*); kangaroo rat (*Dipodomys deserti*); musk rat (*Ondatra* zibethica); pack rat (*Neotoma*); wood rat; sand rat; gerbil; water rat, water vole (*Hydromys chrysogaster*); House mouse (*Mus musculus*); Naked mole rat (*Heterocephalus glaber*); Eurasian red squirrel (*Sciurus vulgaris*); Long-tailed *chinchilla* (*Chinchilla lanigera*); Guinea pig (*Cavia porcellus*); Coypu (*Myocastor coypus*); Capybara (*Hydrochoerus hydrochaeris*); gundis (Hystricomorpha; Ctenodactylus); brush-tailed porcupines (*Atherurus*); mountain degus (*Octodontomys*); North American porcupines (*Erethizon*); guinea pigs (*Cavia*); Sciuromorpha; mountain beavers (*Aplodontia*); New World flying squirrels (*Glaucomys*); chipmunks (*Tamias*); beavers (Castorimorpha; Castor); kangaroo rats (*Dipodomys*); pocket gophers (*Thomomys*); Myodonta; Muroidea; deer mice (*Peromyscus*); true mice (*Mus*); Dipodoidea; birch mice (*Sicista*); jumping mice (*Zapus*); pygmy jerboas (*Cardiocranius*); springhares (Pedetscidae); true gophers (Geomyidae); Laotian rock rat (incertae sedis Diatomyidae); African mole rats (Bathyergidae); giant hutias (Heptaxodontidae); chinchillas, viscachas (Chinchillidae); mouse-like hamsters (Calomyscidae); hamsters, New World rats and mice, muskrats, voles, lemmings (Cricetidae); crested rat (Muridae); climbing mice, rock mice, white-tailed rat, *Malagasy* rats and mice (Nesomyidae); mole rats, bamboo rats, zokors (Spalacidae); and spiny dormice (Platacanthomyidae).

7. A method for repelling rodents, the method comprising applying a polycyclic quinone to a substrate at a level ranging from 5-40 pounds per acre to create a polycyclic quinone barrier that provides a rodent repellency level of at least 80%, wherein the substrate comprises an agricultural or food surface.

8. The method of claim 7 wherein the polycyclic quinone is an anthraquinone.

9. The method of claim 8 wherein the anthraquinone is 9,10 anthraquinone.

10. The method of claim 7 wherein the substrate is selected from the group consisting of agricultural crops, crop seeds, and the ground and ground coverings beneath which roots, tubers and other subsoil agricultural crops grow.

11. The method of claim 7 wherein the agricultural crop comprises sugar cane, maize, rice, wheat, potatoes, sugar beet, soybeans, cassava, tomatoes, barley, cereals, vegetables, melons, roots, tubers, milk, fruit, meat, oilcrops, fish, eggs, pulses, and vegetable fiber.

12. The method of claim 7 wherein the rodents are selected from the group consisting of the entire Rotentia family.

13. The method of claim 7 wherein the rodents are selected from the group consisting of mice and voles, or field mice and meadow mice (Cricetidae); house mice, wood mice, black rats and brown rats (Muridae); deer mice (*Peromyscus*); ground squirrels, tree squirrels, flying squirrels, marmots and prairie dogs (Sciuridae)); pocket gophers (Geomyidae); mountain beaver (Aplodontidae); kangaroo rats, kangaroo mice and pocket mice (Heteromyidae); beavers (Castoridae); scaly-tailed squirrels (Anomaluridae); springhaas (Pedetidae); mole rats (Spalacidae and Bathyergidae); bamboo rats (Rhizomyidae); dormice (Gliridae, Platacanthomyidae and Seleviniidae); jumping mice (Zapodidae); jerboas (Dipodidae); porcupines (Hystricidae and Erethizontidae); cavies (Caviidae); capybara (Hydrochoeridae); pacaranas (Dinomyidae); agoutis and pacas (Dasyproctidae and Agoutidae); chinchillas and vizcachas (Chinchillidae); hutias (Capromyidae); nutria (Myocastoridae); hedge rats and octodonts (Octodontidae); tuco-tucos (Ctenomyidae); *chinchilla* rats (Abrocomidae); spiny rats (Echimyidae); cane rats (Thryonomyidae); dassie rats (Petromuridae); spring hare (Pedetidae) and gundis (Ctenodactylidae); Murinae (Old World rats) and the family Cricetinae (New World rats) both of the order Rodentia; black rat (*Rattus rattus*); brown rat (*Rattus norvegicus*); kangaroo rat (*Dipodomys deserti*); musk rat (*Ondatra* zibethica); pack rat (*Neotoma*); wood rat; sand rat; gerbil; water rat, water vole (*Hydromys chrysogaster*); House mouse (*Mus musculus*); Naked mole rat (*Heterocephalus glaber*); Eurasian red squirrel (*Sciurus* vulgaris); Long-tailed *chinchilla* (*Chinchilla lanigera*); Guinea pig (*Cavia porcellus*); Coypu (*Myocastor coypus*); Capybara (*Hydrochoerus hydrochaeris*); gundis (Hystricomorpha; Ctenodactylus); brush-tailed porcupines (*Atherurus*); mountain degus (*Octodontomys*); North American porcupines (*Erethizon*); guinea pigs (*Cavia*); Sciuromorpha; mountain beavers (*Aplodontia*); New World flying squirrels (*Glaucomys*); chipmunks (*Tamias*); beavers (Castorimorpha; Castor); kangaroo rats (*Dipodomys*); pocket gophers (*Thomomys*); Myodonta; Muroidea; deer mice (*Peromyscus*); true mice (*Mus*); Dipodoidea; birch mice (*Sicista*); jumping mice (*Zapus*); pygmy jerboas (*Cardiocranius*); springhares (Pedetscidae); true gophers (Geomyidae); Laotian rock rat (incertae sedis Diatomyidae); African mole rats (Bathyergidae); giant hutias (Heptaxodontidae); chinchillas, viscachas (Chinchillidae); mouse-like hamsters (Calomyscidae); hamsters, New World rats and mice, muskrats, voles, lemmings (Cricetidae); crested rat (Muridae); climbing mice, rock mice, white-tailed rat, *Malagasy* rats and mice (Nesomyidae); mole rats, bamboo rats, zokors (Spalacidae); and spiny dormice (Platacanthomyidae).

14. The method of claim 1 wherein the polycyclic quionone is applied by painting said polycyclic quinone onto said substrate.

15. A method for repelling rodents, the method comprising applying a polycyclic quinone to a substrate at a level ranging from 200-2000 grams per square meter to create a polycyclic quinone barrier that provides a rodent repellency level of at least 80%, wherein the substrate comprises vegetation.

16. The method of claim 15 wherein the polycyclic quinone is an anthraquinone.

17. The method of claim 16 wherein the anthraquinone is 9,10 anthraquinone.

18. The method of claim 15 wherein the vegetation is selected from the group consisting of assemblages of plant species, agricultural systems, horticultural systems, natural and man-made grasslands, forests, trees, trunks of trees, plants and turf.

19. The method of claim 18 wherein the polycyclic quionone is applied by painting said polycyclic quinone onto said one or more trunks of trees.

20. The method claim 15 wherein the method further prevents girdling of said one of more trunks of trees by a rodent.

* * * * *

UNITED STATES PATENT AND TRADEMARK OFFICE
CERTIFICATE OF CORRECTION

PATENT NO. : 9,999,220 B2
APPLICATION NO. : 14/595718
DATED : June 19, 2018
INVENTOR(S) : Kenneth E. Ballinger and Scott John Werner It is certified that error appears in the above-identified patent and that said Letters Patent is hereby corrected as shown below:

In the Claims

Claim 5:
Column 14, Line 5, delete "Rotentia" and replace it with "Rodentia".

Claim 11:
Column 15, Line 7, delete "oilcrops" and replace it with "oil crops".

Claim 12:
Column 15, Line 10, delete "Rotentia" and replace it with "Rodentia".

Claim 14:
Column 16, Line 18-19, delete "qui-onone" and replace it with "quinone".

Claim 19:
Column 16, Line 37, delete "quionone" and replace it with "quinone".

Signed and Sealed this
Fourth Day of September, 2018

Andrei Iancu
*Director of the United States Patent and Trademark Office*